(12) United States Patent
Dungan

(10) Patent No.: US 9,380,895 B2
(45) Date of Patent: Jul. 5, 2016

(54) SEASONAL MEMORY FOAM PILLOW

(71) Applicant: Gabriel Dungan, Asheville, NC (US)

(72) Inventor: Gabriel Dungan, Asheville, NC (US)

( * ) Notice: Subject to any disclaimer, the term of this patent is extended or adjusted under 35 U.S.C. 154(b) by 0 days.

(21) Appl. No.: 14/453,899

(22) Filed: Aug. 7, 2014

(65) Prior Publication Data
US 2015/0074911 A1  Mar. 19, 2015

Related U.S. Application Data

(63) Continuation-in-part of application No. 13/960,993, filed on Aug. 7, 2013, now abandoned.

(51) Int. Cl.
*A47G 9/10* (2006.01)

(52) U.S. Cl.
CPC ............... *A47G 9/1036* (2013.01); *A47G 9/10* (2013.01); *A47G 2009/1018* (2013.01)

(58) Field of Classification Search
CPC ............ A47G 9/10; A47G 2009/1018; A47G 9/1036; A47G 9/0238; A47G 9/0253; A47G 9/0207; A47G 9/0215; A47C 7/383; A47C 21/048; A47C 21/042; A47C 21/046
USPC ............. 5/644, 636, 639, 640, 645, 490, 654, 5/655.5, 657, 909, 421
See application file for complete search history.

(56) References Cited

U.S. PATENT DOCUMENTS

| | | | |
|---|---|---|---|
| 2,944,266 A | 7/1960 | Wertheimer | |
| 3,411,164 A * | 11/1968 | Sumergrade | A47G 9/10 5/644 |
| 3,443,267 A | 5/1969 | Schuckman | |
| 3,648,469 A | 3/1972 | Chapman | |
| 4,173,048 A | 11/1979 | Varaney | |
| 4,783,866 A | 11/1988 | Simmons et al. | |
| 4,858,259 A * | 8/1989 | Simmons | A47G 9/1036 5/644 |
| 4,887,326 A * | 12/1989 | O'Brien | A47G 9/1036 5/421 |
| 5,163,194 A * | 11/1992 | Dixon | A47G 9/1081 5/636 |
| 5,545,199 A * | 8/1996 | Hudson | A47G 9/1036 5/421 |
| 5,916,088 A | 6/1999 | Gueli | |
| 6,026,330 A | 2/2000 | Chuang | |
| 6,182,312 B1 * | 2/2001 | Walpin | A47G 9/10 5/636 |
| 6,317,908 B1 * | 11/2001 | Walpin | A47G 9/10 5/636 |
| 6,408,467 B2 * | 6/2002 | Walpin | 5/636 |
| 6,622,325 B1 | 9/2003 | Garza | |
| 6,645,235 B1 | 11/2003 | Blackwell | |
| D517,698 S | 3/2006 | Savage | |
| 7,865,987 B2 * | 1/2011 | Deetsch | A47C 16/00 2/468 |
| 8,307,482 B2 * | 11/2012 | Gladney | A47C 27/148 5/655.5 |
| 8,382,692 B1 * | 2/2013 | Chao | A47C 7/383 128/845 |

(Continued)

*Primary Examiner* — Robert G Santos
(74) *Attorney, Agent, or Firm* — Southeast IP Group, LLC; Thomas L. Moses

(57) ABSTRACT

A personal seasonal pillow for accommodating different temperatures occurring during different seasons is disclosed comprising a cool side and a warm side opposite the cool side. A gel layer is associated with the cool side containing a fluid gel, and a layer of insulating fill is associated with the warm side. A cool side indicator is associated with the cool side; and a warm side indicator is associated with the warm side whereby the person may easily identify the desired side.

19 Claims, 4 Drawing Sheets

(56) References Cited

U.S. PATENT DOCUMENTS

| | | | |
|---|---|---|---|
| 8,438,679 B2* | 5/2013 | Wootten, Jr. | A47G 9/0246 5/482 |
| 8,448,273 B2* | 5/2013 | Walker | A47G 9/0253 5/413 R |
| 8,646,134 B1* | 2/2014 | Alletto, Jr. | A47G 9/10 5/490 |
| 8,887,332 B2* | 11/2014 | Alletto | A47G 9/10 5/490 |
| 9,015,883 B2* | 4/2015 | Alletto | A47G 9/1036 5/490 |
| 9,204,731 B2* | 12/2015 | Corodemus | A47G 9/0246 |
| 9,289,082 B1* | 3/2016 | White | A47G 9/10 |
| 2001/0018777 A1* | 9/2001 | Walpin | A47G 9/10 5/636 |
| 2004/0098806 A1* | 5/2004 | Stender | A47C 7/021 5/654 |
| 2006/0112487 A1* | 6/2006 | Taylor | A47G 9/0253 5/490 |
| 2007/0056108 A1 | 3/2007 | Nikolopoulos | |
| 2007/0226911 A1* | 10/2007 | Gladney | A47C 27/148 5/691 |
| 2008/0271249 A1* | 11/2008 | Deetsch | A47C 16/00 5/640 |
| 2009/0205134 A1* | 8/2009 | Wootten, Jr. | A47G 9/0246 5/488 |
| 2010/0005595 A1* | 1/2010 | Gladney | A47C 27/148 5/691 |
| 2010/0139002 A1* | 6/2010 | Walker | A47G 9/10 5/636 |
| 2010/0237082 A1* | 9/2010 | Fernandez | A47C 7/021 220/592.17 |
| 2012/0180225 A1* | 7/2012 | Gladney | A47C 27/148 5/740 |
| 2012/0186022 A1 | 7/2012 | Navarro | |
| 2013/0247297 A1* | 9/2013 | Wootten, Jr. | A47G 9/0246 5/499 |
| 2014/0096323 A1* | 4/2014 | Alletto | A47G 9/10 5/644 |
| 2014/0189955 A1* | 7/2014 | Alletto, Jr. | A47G 9/1027 5/636 |
| 2014/0208518 A1* | 7/2014 | Corodemus | A47G 9/0246 5/691 |
| 2014/0317850 A1* | 10/2014 | Alletto | A47G 9/10 5/638 |
| 2015/0040324 A1* | 2/2015 | Dungan | A47G 9/1036 5/644 |
| 2015/0074911 A1* | 3/2015 | Dungan | A47G 9/1036 5/636 |
| 2016/0058216 A1* | 3/2016 | White | A47G 9/10 5/636 |
| 2016/0073800 A1* | 3/2016 | Ives | A47G 9/10 5/636 |
| 2016/0081487 A1* | 3/2016 | Corodemus | A47C 27/085 5/636 |

* cited by examiner

SEASONAL MEMORY FOAM PILLOW

BACKGROUND OF THE INVENTION

The invention relates to a bedroom pillow and the like, and particularly to the construction of a reversible pillow that seeks to enhance comfort based on the seasonality of sleeping conditions.

Sleep comfort is a field that continues to draw attention given the lack of sleep suffered by many people in today's society. Given the changes in temperature throughout the year in many geographic locations, a need exists to provide a pillow that suits these changes in temperature. Many people sweat during the night creating a less comfortable sleeping experience around their head and neck area. Conversely, the cooler temperatures during the year create a need for warm materials for more insulation. Prior attempts to provide pillows with different comfort characteristics include US published application 20070056108 A1 (Nikolopoulos) disclosing a face rest with gel fill that may be adjusted to a temperature to heat or cool a user's face. U.S. Pat. No. 2,944,266 A (Wertheimer) shows a pillow or cushion that has one section filled with sponge or foam rubber and a second section filled with down or the like. U.S. Pat. No. 3,443,267 A (Schuckman) shows a pillow that includes compartment filled with down feathers and a compartment filled with whole feathers. U.S. Pat. No. 4,173,048 A (Varaney) shows a pillow configuration that includes batt material and foam material contained within opposite sides thereof of a pillow. The batt material provides heat retention during cool weather. The other side can be employed during warm weather when a cooler side is needed. U.S. Pat. No. 4,783,866 A (Simmons et al.) and U.S. Pat. No. 4,858,259 A (Simmons et al.) show a therapy pillow with a removable therapeutic gel pack. U.S. Pat. No. 5,916,088 A (Gueli) shows a cooling beach pillow that includes a layer of thermally conductive gel material. U.S. Pat. No. 6,026,330 A (Chuang) shows a multi-function pillow. U.S. Pat. No. 6,622,325 B1 (Garza) shows a facial fatigue reducing pillow construction that includes an upper portion of foam material and a lower batting filled portion. U.S. Pat. No. 6,645,235 B1 (Blackwell) shows a hot/cold pack therapeutic device that includes a thermally conductive material for facilitating heat transfer. U.S. design Pat. D517698 S (Savage) shows the ornamental design for a cold pillow. U.S. Pat. No. 3,648,469 A (Chapman) shows a thermoelectric pillow. US published application 20120186022 A1 (Navarro) shows a pillow that includes a polyurethane foam layer and a fiber layer. The pillow may include an optional layer of gel between the two surface layers.

However, in spite of the prior efforts, a truly seasonal pillow having reversible sides providing effective warming and cooling has not been provided. Thus, it can be seen that a pillow which aids in mitigating temperature changes and other associated comfort challenges is deserving of much consideration.

Accordingly, an object of the present invention is to provide a reversible, seasonal pillow having an effective cooler side and a warmer side.

Another object of the invention is to provide a seasonal pillow having a combination of warming material on one side and a cooling gel layer on the reverse side to provide comfort for temperature changes.

Another object of the invention is to provide a seasonal pillow having a cool side with a contoured gel layer which circulates the gel when a person moves on the pillow to increase a cooling effect Another object of the invention is to provide a seasonal pillow having a cool side and a warm side surrounded by a cover having indicia indicating the warm and cool sides.

SUMMARY OF THE INVENTION

The above objectives are accomplished according to the present invention by providing a personal seasonal pillow for accommodating different seasonal temperatures comprising a reversible pillow having a cool side and a warm side. The cool side includes a gel layer containing a fluid gel for coolness during warmer months. The warm side includes an insulation layer having a fill material for warmth during cooler months. A resilient layer is disposed intermediate the cool and warm layers, and a pillow cover encloses the layers. The resilient layer includes memory foam having a contoured surface contacting the gel layer to enhance circulation of the fluid gel across the cool side when the person moves which allows the fluid gel to circulate across the pillow. The contoured surface includes a series of ridges and channels which create groves in the gel layer. The ridges and channels are curved across the contoured surface and the pillow. The fill includes one of natural feathers, natural down, natural fibers, synthetic fibers, synthetic material, cotton, and a mixture thereof. The gel and resilient layer have a cross-section maximum thickness at a midpoint which tapers from the midpoint to outer edges. The warm layer has a cross-section maximum thickness at a midpoint which tapers from the midpoint to outer edges. In a preferred embodiment, the pillow may include indicators associated with the cover to differentiate the warm and cool sides. The pillow indicators may include spaced piping on the cover having different color indicators. In a simplified embodiment, the cool gel layer and the warm insulated layer may meet at a single edge of piping.

DESCRIPTION OF THE DRAWINGS

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
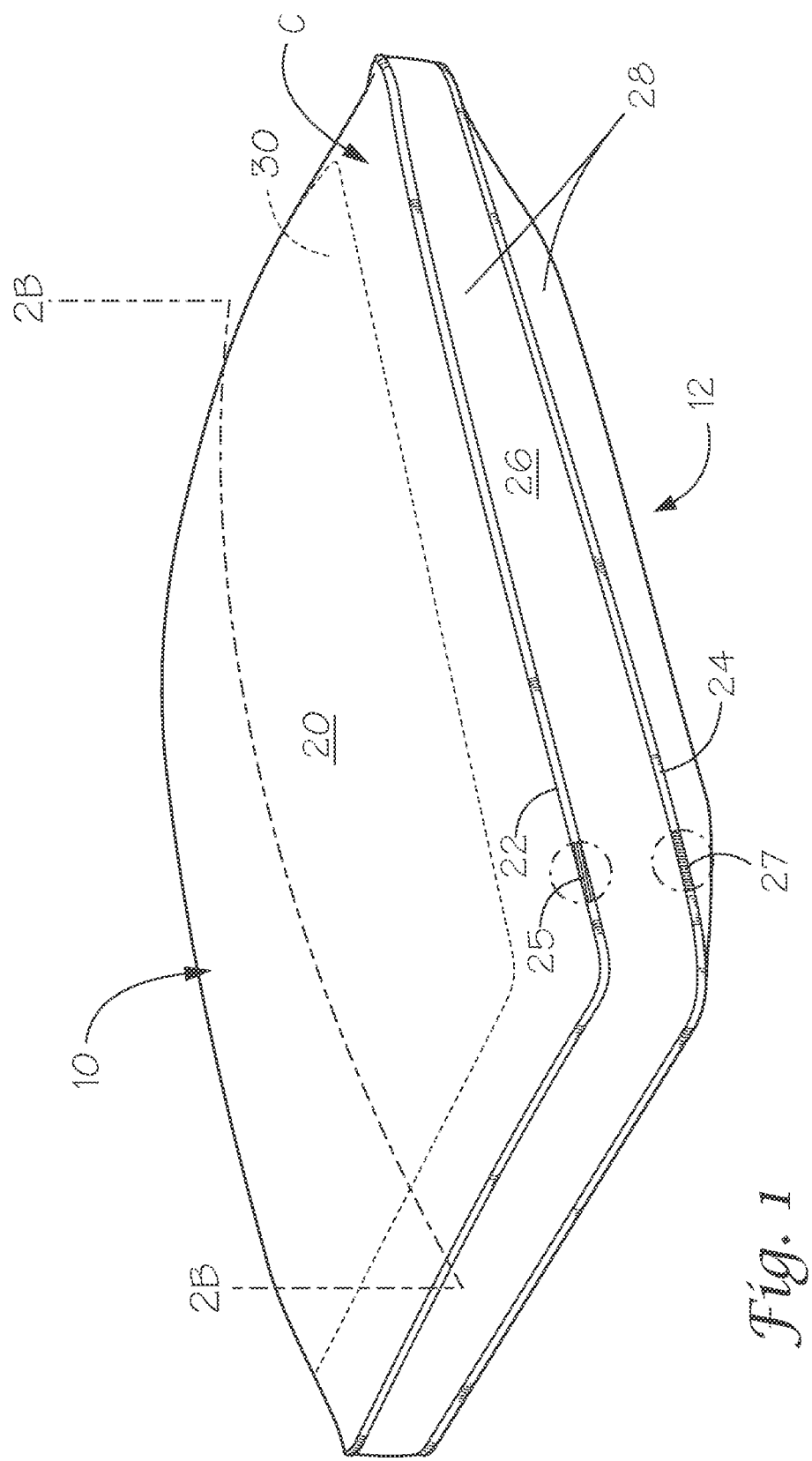
FIG. 1 is a left perspective view of a seasonal pillow constructed according to a preferred embodiment.

Referring now to the drawings, the invention will be described in more detail.

Figure 5:
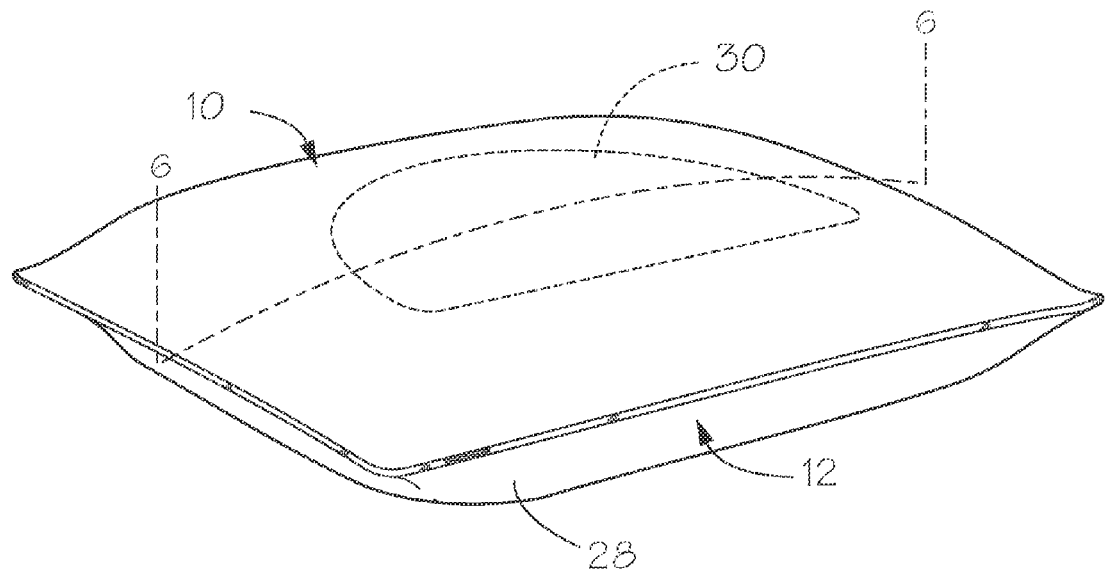
FIG. 5 is a perspective view of a seasonal pillow constructed according to an alternative embodiment.

As can best be seen in FIGS. 1 and 5, a reversible seasonal pillow, generally designated as A, is shown having a two sided option, including a cool side 10 (gel side) to cool the individual, and a warm side 12 (textile fill) to insulate and warm the individual during the cool months. The design of the cool side includes an efficient gel layer, such as a silica gel layer. When the person moves during their sleep, the gel circulates thereby providing renewed coolness. This gel layer 30 may be any desired shape or size, and may partially cover or substantially cover the cool side 10. In a preferred embodiment illustrated by FIG. 1, the gel layer 30 may be rectangular in shape and cover a substantial portion of the cool surface 10. In this embodiment, the user may position his or her head on any portion of the cool side 10 and experience a cooling effect from the gel. Alternatively, a simplified and more cost-efficient gel layer 30 may be employed, whereby the gel may cover only the portion of the pillow where the user will most likely place his or her head. FIG. 5 illustrates a gel layer 30 that is preferably a half-moon shape and generally centrally located on the cool layer 10, covering approximately one third of the pillow surface. Although any shape may be used such as square, rectangle, circle, oval, and the like, the half-moon shape is preferable as it allows for contouring of the shape of a user's head. On the reverse side of the pillow, the warm side 12 includes an insulating layer filled with one of natural feathers, natural down, natural fiber, cotton fill, denier microfiber, and mixtures thereof. The idea is that during the cooler months, warm side 12 will provide a more appropriate insulation and comfort for these weather conditions. In the warmer months, the cool side 10 will provide a more appropriate cooling layer for comfort during these weather conditions.

Figure 2A:
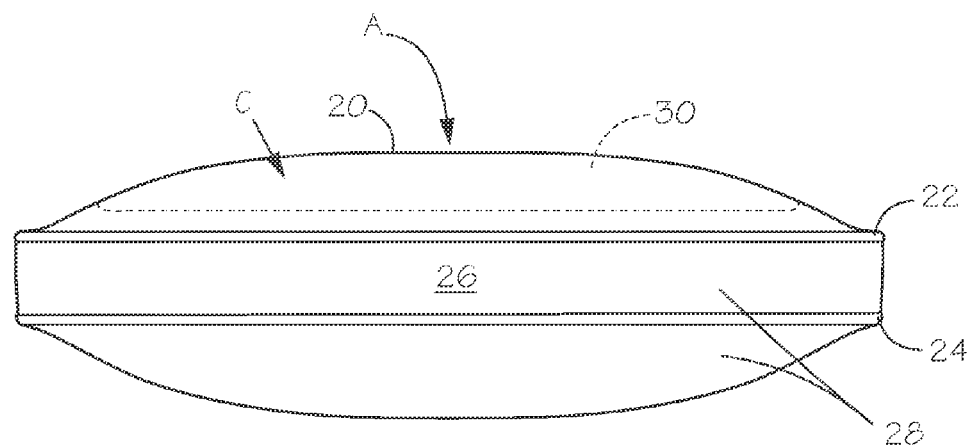
FIG. 2A is an end elevation of the pillow of FIG. 1.
Figure 2B:
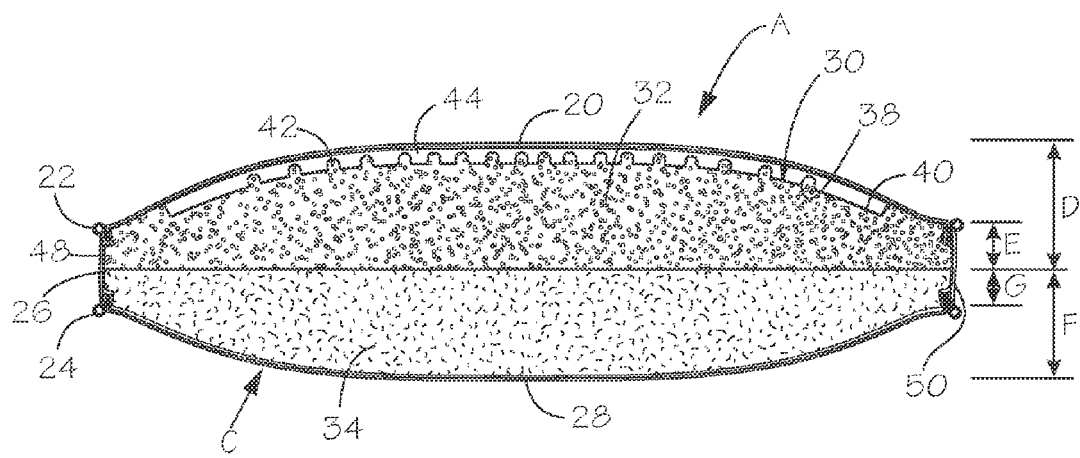
FIG. 2B is a cross-sectional view taken along line 2B-2B.

Referring now in more detail, as can best be seen in FIGS. 2A and 2B, seasonal pillow A includes a cover C having two parts, a first cover part 20 including a cover which may be bounded by piping 22 on the cool side, and a second cover part 28 preferably including a gusset 26 panel between piping 22 and a piping 24 and continuing to the other side of the pillow and terminating at piping 22. Indicators 25 and 27 may be provided on the cover to indicate the cool and warm sides. By making piping 22 a cool color, such as blue, and making piping 24 a warm color, such as red, the colors are indications of the cool side and the warm side. Of course, any different colors or indicia can be used if effective to indicate the cool and warm sides, and all or a portion of the piping may include the indicator. Alternatively, the gusset panel and dual piping may be optional. FIG. 5 shows an alternative embodiment whereby the first cover part 20 and second cover part 28 may be bounded together by a single piping, omitting the gusset. First part 20 of the cool side of cover C preferably made from a breathable, moisture-wicking fabric such as CoolMax® (trademark of Invista) or similar "dri" fabric in order for the person to be able to experience the cooling effect more easily. The second cover part 28 may be any suitable bedding fabric, natural, synthetic, or mixtures. Preferably, cotton is used. The cover may be woven or non-woven.

Figure 3:
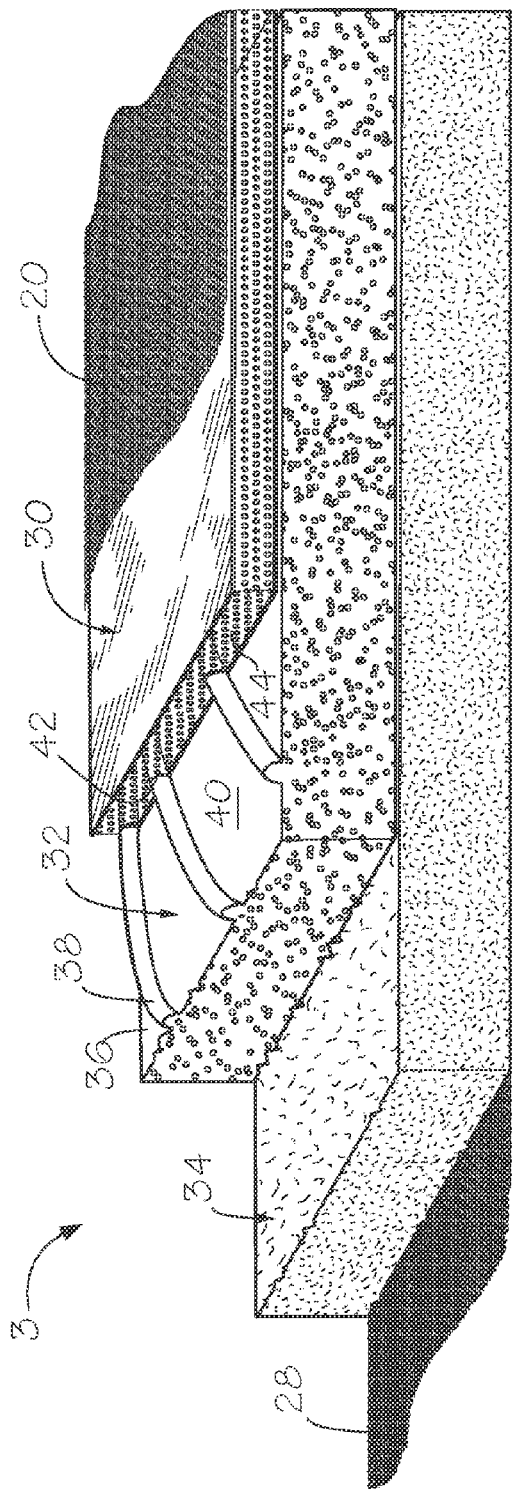
FIG. 3 is a perspective view of a seasonal pillow constructed according to a preferred embodiment taken from FIG. 4 illustrating the pillow layers in cross-section and longitudinal section.
Figure 6:
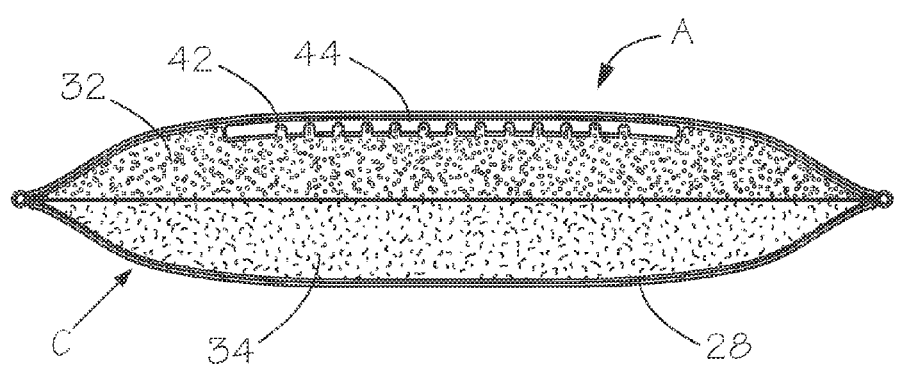
FIG. 6 is a cross-sectional view of an alternative embodiment taken along lines 5-5.

Referring now to FIGS. 2B, 3, and 6, the invention will be described in more detail referring to the cross-section and longitudinal views. FIGS. 2B and 6 show two embodiments of the seasonal pillow in cross-section from the top to the bottom of the pillow, including cover 20, gel layer 30, resilient or memory foam layer 32, textile fill layer 34, and bottom cover 28. Foam layer 32 is contoured to form corresponding opposite contours in the gel layer 30. For this purpose, a top 36 of the foam layer is contoured by a series of ridges 38 and channels 40 which press into the gel layer to create a series of spiral grooves 42 in the gel layer. The spiral grooves allow the fluid gel to circulate across the pillow as the sleeper changes position. Other contouring or shape of the foam top 36 may be used to achieve the same benefits. Foam layer 32 is preferable, a suitable resilient polyurethane foam, such as memory foam. Latex foam may also be used in some applications.

Textile fill layer 34 may include any suitable textile or other fill material including natural feathers, natural down, natural fibers, cotton filling, denier microfiber, and mixtures of two or more thereof. The drawing dimensions of the layers are not necessarily to scale but are for illustration purposes. In one embodiment of the invention, gel layer 30 and memory foam layer 32 have a cross-section which varies at a midpoint generally between 2.5 and 4.0 inches. Opposing tapered edges 48 of the layers very in thickness, generally between 2.0 and 3.25 inches. Insulating layer 34 preferably has a thickness at its midpoint of between 2.5 and 3.5 inches. Tapered opposing edges 50 have a thickness of generally between 2.0 and 3.5.

Figure 4:
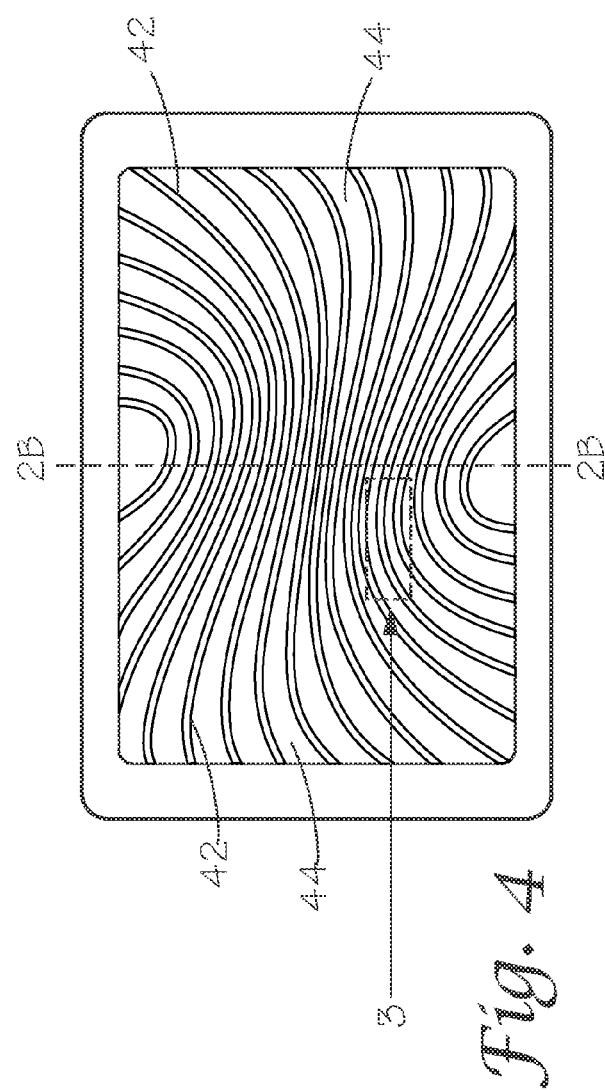
FIG. 4 is a top plan view of a gel layer having ridges and channels spiraled across the pillow for enhanced cooling constructed according to a preferred embodiment.

It is to be understood that the seasonal pillow may be modified or constructed in alternative embodiments. The pillow may be fabricated to target a high-end consumer, or modified to adjust manufacturing costs and meet a price point best for mass-marketing. The gel layer 30 may be any shape or size, as desired and may cover a substantial or only a partial portion of the surface layer. Additionally, the fill layer 34 may be any single or combination of desired textiles as described above. Referring now to FIG. 5, in one alternative embodiment, the pillow may include a cover 20 and 28 covering the cool layer 10 and warm layer 12, respectively. In a preferred embodiment shown by FIGS. 1 and 4, the gel layer 30 may be rectangular in shape and substantially covering the surface of the cool, resilient layer 10. Alternatively, the gel layer 30, as shown in FIG. 5, may be a half-moon shape covering a smaller portion of the cool, resilient layer 10.

While the preferred embodiment of the invention has been described using specific terms, such description is for illustrative purposed only, and it is to be understood that changes and variations may be made without departing from the spirit or scope of the following claims.

What is claimed is:

1. A personal seasonal pillow for accommodating different seasonal temperatures comprising:
    a reversible pillow having a cool side and a warm side;
    said cool side including a gel layer containing a fluid gel for coolness during warmer months; and
    said warm side including an insulation layer having a fill material for warmth during cooler months;
    a resilient layer intermediate said cool and warm sides, wherein said resilient layer includes memory foam having a contoured surface contacting said gel layer to enhance circulation of the fluid gel across the cool side when the person moves;
    wherein said contoured surface of the memory foam layer creates grooves in the gel layer which allow the fluid gel to circulate across the pillow;
    wherein said contoured surface of said memory foam includes a series of ridges and channels which create said grooves in said gel layer; and
    a pillow cover for enclosing said layers.

2. The pillow of claim 1 wherein said ridges and channels are curved across said contoured surface and said pillow.

3. The pillow of claim 1 wherein said fill material includes one of natural feathers, natural down, natural fibers, synthetic fibers, synthetic material, cotton, and a mixture of two or more thereof.

4. The pillow of claim 1 wherein the gel and resilient layers each have a cross-section thickness at a midpoint which is generally between 2.5 and 4 inches.

5. The pillow of claim 4 wherein the gel and resilient layers each taper from said midpoint to outer edges having a thickness generally between 2.0 and 3.25 inches.

6. The pillow of claim 1 wherein the insulation layer has a cross-section thickness at a midpoint generally between 2.5 and 3.5 inches.

7. The pillow of claim 6 wherein the insulation layer tapers from said midpoint to outer edges which have a thickness generally between 2.0 and 3.5 inches.

8. The pillow of claim 1 including pillow indicators associated with said cover differentiating the warm and cool sides.

9. The pillow of claim 8 wherein said pillow indicators include spaced piping on said cover having different color indicators on at least a portion thereof.

10. The pillow of claim 1 wherein said cool side and said warm side are bound by a single piping.

11. The pillow of claim 1 wherein said gel layer covers a substantial portion of said cool side.

12. The pillow of claim 1 wherein said gel layer is generally centrally located and covers less than half of the surface area of said cool side.

13. The pillow of claim 12 wherein the shape of said gel layer is selected from the group consisting of half-moon, circle, oval, square, and rectangle.

14. A personal seasonal pillow for accommodating different temperatures occurring during different seasons comprising:
   a cool side and a warm side opposite said cool side;
   a gel layer containing a fluid gel associated with said cool side, and wherein said gel layer includes a plurality of grooves through which said gel fluid may circulate as the individual moves;
   a layer of fill associated with said warm side;
   a cool side indicator associated with said cool side;
   a warm side indicator associated with said warm side whereby a person may easily identify the desired side; and
   a resilient foam layer having a contoured surface pressing against said gel layer to create the grooves in said gel layer.

15. The apparatus of claim 14 wherein said contoured surface of said foam layer includes ridges and channels which create said grooves in said gel layer.

16. The pillow of claim 14 including a cover surrounding said cool and warm sides including a bottom cover, a top cover, and a gusset panel joining said bottom and top covers.

17. The pillow of claim 16 including a first piping joining said top cover and said gusset panel indicating the cool side of the pillow, and a second piping joining said bottom cover and said gusset panel to indicate the warm side of the pillow.

18. The pillow of claim 17 the first piping includes a blue color and said second piping includes a red color.

19. The pillow of claim 16 wherein said top cover includes breathable moisture-wicking material.

* * * * *